United States Patent [19]
Calello et al.

[11] Patent Number: 5,993,837
[45] Date of Patent: Nov. 30, 1999

[54] COMPOSITIONS FOR APPLICATION TO KERATINOUS SUBSTRATES AND A METHOD FOR STRENGTHENING SUCH SUBSTRATES

[75] Inventors: Joseph Frank Calello, Union; Anjali Abhimanyu Patil, Westfield; David Allen Porter, Phillipsburg; Robert Walter Sandewicz, Spotswood, all of N.J.; Douglas Dean Schoon, Laguna Niguel, Calif.

[73] Assignee: Revlon Consumer Products, NY, N.Y.

[21] Appl. No.: 09/170,244

[22] Filed: Oct. 13, 1998

Related U.S. Application Data

[60] Provisional application No. 60/097,629, Aug. 24, 1998.
[51] Int. Cl.⁶ .............................. A61K 6/00; A61K 7/00; A61K 7/04
[52] U.S. Cl. .......................... 424/401; 424/61; 424/70.1; 514/937; 514/938
[58] Field of Search ........................... 424/401, 61, 70.1; 514/937, 938

[56] References Cited

U.S. PATENT DOCUMENTS

| | | | |
|---|---|---|---|
| 3,349,000 | 10/1967 | Joos | 167/85 |
| 3,725,525 | 4/1973 | Joos | 424/61 |
| 3,773,056 | 11/1973 | Kalopissis | 132/7 |
| 4,240,450 | 12/1980 | Grollier et al. | 132/7 |
| 4,323,553 | 4/1982 | Bouillon | 424/61 |
| 4,381,294 | 4/1983 | Bouillon | 424/61 |
| 4,547,363 | 10/1985 | Joos | 424/61 |
| 5,102,654 | 4/1992 | Castrogiovanni | 424/61 |
| 5,308,609 | 5/1994 | Etheredge | 424/61 |
| 5,478,551 | 12/1995 | Busch | 424/61 |
| 5,490,980 | 2/1996 | Richardson | 424/94.6 |
| 5,785,959 | 7/1998 | Wolf | 424/61 |

*Primary Examiner*—Thurman K. Page
*Assistant Examiner*—Sharon Howard
*Attorney, Agent, or Firm*—Julie Blackburn

[57] ABSTRACT

A composition for application to solid, keratinous surfaces comprising 0.01–80% of a thio-free keratinous protein cross-linking agent, 1–75% of a solvent, and 0.01–35% of a film former, and a method for strenghthening keratinous surfaces by applying the composition of the invention.

13 Claims, No Drawings

COMPOSITIONS FOR APPLICATION TO KERATINOUS SUBSTRATES AND A METHOD FOR STRENGTHENING SUCH SUBSTRATES

RELATED APPLICATIONS

This application is a continuation of provisional patent application Ser. No. 60/097,629, filed Aug. 24, 1998.

TECHNICAL FIELD

The invention is in the field of compositions for application to solid keratinous substrates such as nails or hair, and a method for strengthening such substrates.

BACKGROUND OF THE INVENTION

Consumers are constantly concerned about brittle, chipped, nails and dry, flyaway hair. Particularly for nails, there are many products which claim to strengthen nails and promote the growth of strong, healthy nails. For example, it is well known that formaldehyde and derivatives thereof are effective in strengthening nail keratin because such compounds are said to cross-link the proteins found in nail keratin. However, formaldehyde in particular, is generally considered undesireable for use on nails because it is known to be a sensitizer, particularly if used in the concentrations which are necessary to achieve appreciable nail hardening.

U.S. Pat. No. 3,349,000 teaches a method for treating human nails and hair with dimethylol thiourea, which is said to improve strength and elasticity. The patentee teaches that if compositions containing dimethylol thiourea are applied to nails or hair, these substrates are more resistant to cracking, splitting, laminating, or similar problems. While these compositions may work well, dimethylol thiourea contains sulfur, thus may have an unpleasant odor which consumers find unattractive.

U.S. Pat. No. 4,323,553 also teaches compositions used to strengthen and revitalize brittle or damaged nails, which contain 2-benzylthio ethylamine, another sulfur containing compound. This compound also contains sulfur and may provide an odor which consumers find unattractive.

U.S. Pat. No. 4,547,363 teaches a two part composition for strengthening nails. The first composition contains dimethylol ethylene thiourea and the second composition contains a polymerizable catalyst which contains an acid such as hydrochloric acid. The two compositions are mixed and applied to nails. This system is inconvenient because it requires the mixture of two separate compositions prior to use, which makes it more difficult for the consumer to use.

U.S. Pat. No. 5,785,959 teaches nail strengthening compositions which contain a permeation/binding agent, a thio cross-linking agent, and a chelating agent.

There is a need for compositions which further strengthen solid keratinous surfaces and, particularly with respect to fingernails, provide improved hardness, strength, and elasticity to the nail surface.

BACKGROUND OF THE INVENTION

The invention comprises a composition for application to solid, keratinous surfaces comprising, by weight of the total composition:

0.01–80% of a thio-free keratinous protein cross-linking agent,
1–75% of a solvent, and
0.01–35% of a film former.

The invention further comprises a water/oil emulsion for application to solid, keratinous surfaces comprising, by weight of the total composition:

0.01–80% of a thio-free keratinous protein cross-linking agent,
1–95% water,
1–75% oil.

The invention also comprises a method for strengthening solid keratinous surfaces comprising applying to said surfaces a composition comprising, by weight of the total composition:

0.01–80% of a keratinous protein cross-linking agent,
1–75% of a solvent, and
0.01–35% of a film former.

Detailed Description

All percentages mentioned herein are percentages by weight unless otherwise indicated. The compositions of the invention are used to strengthen solid keratinous surfaces and contain the following ingredients.

Keratinous Protein Cross-Linking Agent

The compositions of the invention comprise 0.01–80%, preferably 0.1–60%, more preferably 0.1–15% of a keratinous protein cross-linking agent. The term "keratinous protein cross-linking agent", means a compound free of thio groups, which is capable of cross-linking the proteins which are found in the solid keratinous surface, i.e. the proteins found in hair or nails. The term "free of thio groups" means that the compound does not contain any sulfur atoms. Generally, the cross-linking agent functions by reacting with nucleophilic residues which may be found in the keratin proteins, i.e. nitrogen, oxygen, or sulfur. Some non-limiting examples of how the keratinous protein cross-linking agent may react with the keratinous protein are set forth below:

(I) with thiol residues, i.e. as found in cysteine, or any free hydroxyl or acid functionality within the protein structure, or
(II) with terminal amine groups on protein chains, or
(III) with amide linkages within protein backbone.

The thio-free keratinaceous protein cross-linking agent used in the methods and compositions of the invention has the general formula:

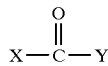

wherein X and Y are each independently halogen, $C_{1-20}$ straight or branched chain alkyl, alkoxy, aryloxy, or NRR' wherein R and R' are each independently hydrogen, halogen, $C_{1-20}$ straight or branched chain alkyl, alkoxy, aryloxy, with the proviso that at least one of R or R' is an alkyl group. Preferred are compounds wherein R is H, and R' is a $C_{1-10}$ straight or branched chain alkyl, preferably a $C_{1-4}$ alkyl, more preferably methyl. Particularly preferred is 1,3-dimethyl urea.

Solvent

The compositions of the invention comprise 1–75%, preferably 5–60%, more preferably 10–50% of a solvent. The solvent may be aqueous or non-aqueous or a mixture of both types of solvents. Suitable non-aqueous solvents include aliphatic or aromatic ketones such as acetone, diacetone alcohol, dihydroxyacetone, ethyl butyl valerolactone, methyl ethyl ketone, and the like; aliphatic or aromatic alcohols such as methanol, propanol, benzyl alcohol, butoxyethanol, butoxypropanol, butyl alcohol, 3-methyl-3-methoxy-butanol, t-butyl alcohol, butylene glycol, diethylene glycol, abietyl alcohol, propylene carbonate, hexyl alcohol, isopropanol, and the like; glycol ethers; esters formed by the reaction of $C_{1-10}$ alkanols and carboxylic acids, i.e. butyl acetate, ethyl acetate, etc. Preferably the solvent is a mixture of non-aqueous solvents, such as butyl acetate and ethyl acetate.

Other Ingredients

The compositions of the invention may be in the form of a nail enamel composition, a water and oil emulsion treatment compositions for application to the nails, or in another form suitable for application to solid keratinous surfaces such as hair fibers.

Preferably, the compositions of the invention are nail enamel compositions. Such nail enamel compositions may be aqueous or solvent-based, i.e. non-aqueous, and preferably contain other ingredients such as film formers, plasticizers, suspending agents, pigments, pigment stabilizers, preservatives, and the like.

Film Formers

The nail enamel compositions of the invention contain one or more film formers which cause the nail enamel to form a stable film on the nail upon drying. Suggested ranges of film formers are 0.1–60%, preferably 0.5–50%, more preferably 1–45% by weight of the total composition. A wide variety of film formers are suitable.

Cellulosic film formers are widely used, and are suitable for use in the compositions of the invention. Examples of cellulosic film formers include nitrocellulose, cellulose acetate, cellulose acetate butyrate, cellulose acetate isobutyrate, cellulose acetate propionate, cellulose acetate propionate carboxylate, cellulose and the like.

Also suitable as film formers are various polymers such as homo- or copolymers of acrylic acid, methacrylic acid, acrylate, methacrylate, styrene, urethane, and so on. Examples of film forming polymers are homo- and copolymers of monomers having the general formulas set forth below:

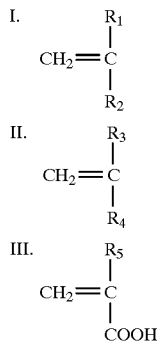

wherein $R_1$, $R_3$, and $R_5$ are each independently H, a $C_{1-30}$ straight or branched chain alkyl, aryl, aralkyl; $R_2$ is a pyrrolidone, or a substituted or unsubstituted aromatic, alicyclic, or bicyclic ring where the substituents are $C_{1-30}$ straight or branched chain alkyl, or COOM wherein M is a $C_{1-30}$ straight or branched chain alkyl, pyrrolidone, or a substituted or unsubstituted aromatic, alicyclic, or bicyclic ring where the substitutents are $C_{1-30}$ straight or branched chain alkyl.

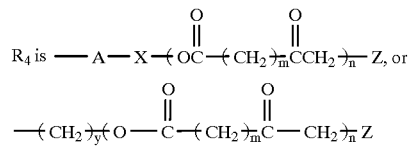

wherein

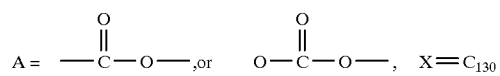

straight or branched chain alkyl, m is 1 to 5, n is 1 to 30, y is 0 to 50; and Z=H or a $C_{1-30}$ straight or branched chain alkyl.

Plasticizers

The nail enamel compositions of the invention may contain 0.01–40%, preferably 0.1–35%, more preferably 0.5–30% by weight of the total composition of one or more plasticizers. A plasticizer acts to make the film formed by the film former more pliable. It is believed that the plasticizer acts by modifying the Van der Waals forces between the molecular chains of the film former. Suitable plasticizers are phthalates such as dibutyl phthalate, dioctyl phthalate, diphenyl phthalate, camphor, dibutyoxy ethyl phthalate, and so on. Also suitable are phosphates such as tricresyl phosphate or triphenyl phosphate; camphor, or castor oil.

Particularly preferred are glyceryl, glycol, or citrate ester plasticizers as disclosed in U.S. Pat. No. 5,145,671, which is hereby incorporated by reference. These plasticizers have the following general formulas:

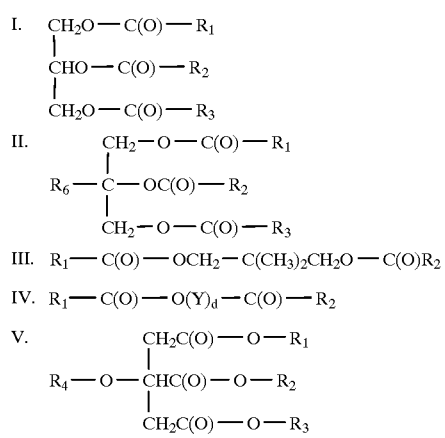

wherein $R_1$, $R_2$, and $R_3$ are the same or different and represent (i) linear or branched chain alkyl having 1 to 35 carbon atoms, cyclic alkyl having 3 to 8 carbon atoms, or linear or branched alkenyl having 2 to 35 carbon atoms, any of the foregoing being unsubstituted or substituted with one, two, or three groups selected from the group consisting of: —CN, —SCN, —OH, —SH, —NH$_2$, —CONH$_2$, and —NO$_2$;

(ii) —X—C(O)O—A or —X—O—C(O)—A in which X is a straight or branched chain alkyl or alkenyl bridge containing up to 8 carbon atoms, or is a phenyl ring —$C_6H_4$—, and A is phenyl, straight or branched alkyl having 1 to 35 carbon atoms, or straught or branched alkylene having 2 to 35 carbon atoms, wherein when X or A is alkyl or alkenyl is it optionally substitued with —CN, —SCN, —$NO_2$, —OH, —SH, —$NH_2$, or $CONH_2$, and wherein when X or A is phenyl it is optionally substituted with one, two, or three substituents selected from the group consisting of —CN, 'SCN, —Cl, —Br, —F, —$OCH_3$, —$OC_2H_5$, —$OC_6H_5$, —CH=$CH_2$, $C_{1-6}$ alkyl, —$CH_2$CH=$CH_2$, —$NO_2$, —$NH_2$, —OH, —SH, and —$SO_2NH_2$;

(iii) a dimer or trimer acyl group; or (iv) BZ;

wherein BZ is a phenyl ring which is unsubstituted; or substituted with one or two groups of the formula —C(O) $OR_5$ wherein $R_5$ is a straight or branched alkyl containing 1 to 35 carbon atoms, or straight or branched alkylene containing 1 to 35 carbon atoms, the alkyl and alkenyl optionally substitued with —CN, —SCN, —$NO_2$, —OH, —SH, —$NH_2$, or —$CONH_2$; or $R_5$ is phenyl, unsubstituted or substituted with one, two or three substituents selected from the group consisting of —CN, —SCN, —Cl, —Br, —F, —$OCH_3$, —$OC_2H_5$, —$OC_6H_5$; —CH=$CH_2$, $C_{1-6}$ alkyl, $CH_2$CH=$CH_2$, $NO_2$, $NH_2$, —OH, —SH, and —$SO_2NH_2$; and wherein d is 1 to 1,000, each Y is ethoxy, isopropoxy, or proposy, R4 is H— or (Alk)—C(O)— wherein (Alk) is straight or branched alkyl containing 1 to 18 carbon atoms or straight or branched alkenyl containing 2 to 18 carbon atoms. Preferably the plasticizer is a Formula I or Formula V compound, or mixtures thereof. Particularly preferred is a plasticizer of Formula I wherein $R_1$, $R_2$, and $R_3$ are each independently a $C_{1-35}$ linear or branched alkyl, or BZ, more specifically, the compounds are glyceryl tribenzoate and glyceryl triacetate. The Formula V compounds are wherein $R_1$, $R_2$, and $R_3$ are each independently a linear or branched alkyl having 1 to 35, preferably 1–10, more preferably 1–4 carbon atoms, most preferably acetyl tributyl citrate.

Pigments

The nail enamel compositions of the invention may be pigmented or clear. If pigmented, generally 0.1–30% by weight of the total composition, preferably 0.5–20%, more preferably 1–15% of pigment is suggested. Pigments suitable for use in nail enamel compositions are well known and include iron oxides, D&C and FD&C colors, titanium dioxide, and the like. The pigments may be treated or coated with agents which modify the surface properties such as silicones. Examples of silicone treated pigments which can be used in the compositions of the invention are set forth in U.S. Pat. No. 4,832,944, which is hereby incorporated by reference.

Suspending Agent

If the nail enamel compositions of the invention contain pigments, it is desireable to also incorporate 0.01–15%, preferably 0.1–10%, more preferably 0.5–5% by weight of the total composition of a suspending agent which acts to suspend the pigments in the formulation. Suitable suspending agents are montmorillonite minerals and derivatives thereof, such as stearalkonium bentonite, hectorites, attapulgite, bentones, and the like, as well as polymeric compounds known as associative thickeners. Suitable associative thickeners generally contain a hydrophilic backbone and hydrophobic side groups. Examples of such thickeners include polyacrylates with hydrophobic side groups, cellulose ethers with hydrophobic side groups, polyurethane thickeners. Examples of hydrophobic side groups are long chain alkyl groups such as dodecyl, hexadecyl, or octadecyl; alkylaryl groups such as octylphenyl or nonyphenyl.

Pigment Stabilizers

If pigments are included in the nail enamel composition, it may be desireable to add one or more organic or inorganic acids to the composition, which will aid in stabilizing pigments so that they do not settle out of the formula. If pigment stabilizers are added, a range of 0.001–5%, preferably 0.005–4%, more preferably 0.010–3% by weight of the total composition is suggested. Suitable inorganic acids are hydrochloric acid, phosphoric acid, sulfuric acid, and the like. Suitable organic acids include hydroxy acids such as citric acid, malic acid, glycolic acid, and the like.

Particularly preferred are non-aqueous nail enamel compositions comprising:

0.01–25% of a keratinous protein cross-linking agent having the general formula:

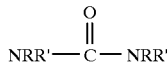

wherein R and R' are each independently H, or $C_{1-20}$ straight or branched chain alkyl with the proviso that at least one of R or R' is an alkyl group, 1–75% of a non-aqueous solvent, and 0.01–35% of a cellulosic film former.

The compositions of the invention also include water-in-oil or oil-in-water emulsion compositions which may be applied to the nails to provide a treatment benefit, preferably before application of nail enamel. These compositions comprise, by weight of the total composition:

0.01–25% of a thio-free keratinous protein cross-linking agent,

1–95% water,

1–75% oil.

In addition, other ingredients may be present, preferably those which provide a treatment benefit.

Oils

Oils may be present, if desired, and suitable ranges are 0.1–60%, preferably 1–50%, more preferably 5–40% oil. Suitable oils include volatile and nonvolatile silicones. The term "volatile" means that the silicone has a vapor pressure of at least 2 mm. of mercury at 20° C. The term "nonvolatile" means that the silicone has a vapor pressure of less than 2 mm. of mercury at 20° C. Suitable volatile silicones may be linear or cyclic. Cyclic volatile silicones have the general formula:

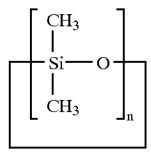

wherein n=3–7, preferably 3–6.

Also suitable are volatile and nonvolatile linear silicones having the general formula:

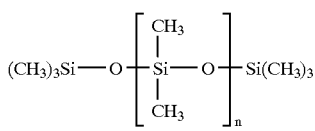

wherein n=0–1,000,000.

Examples of such silicones include cyclomethicone, hexamethyldisiloxane, dimethicone, and the like.

Also suitable are silicone surfactants such as dimethicone copolyol, dimethiconol, and the like, as well as phenyl substituted silicones like phenyl trimethicone, phenyl dimethicone, and so on.

Volatile and nonvolatile paraffinic hydrocarbon fluids such as mineral oil, or $C_{5-40}$ straight or branched chain hydrocarbon fluids are also suitable for the oil ingredient. Examples of volatile paraffinic hydrocarbon fluids are disclosed in U.S. Pat. Nos. 3,439,088 and 3,818,105 which are hereby incorporated by reference. Such paraffinic hydrocarbons include isododecane, isohexadecane, decane, dodecane, and so, on. These types of paraffinic hydrocarbon fluids are sold by Permethyl under the Permethyl tradename.

Preferred oil ingredients are silicones either alone or in combination with nonvolatile paraffinic hydrocarbon fluids.

Vitamins

It may be desireable to add vitamins, and if so 0.01–20%, preferably 0.1–15%, more preferably 0.1–10% vitamins are suggested. Examples of suitable vitamins include vitamin E (tocopherol) vitamin C PMG (also known as magnesium ascorbyl phosphate), thiamine, pyridoxine, nicotinamide, vitamin D, or mixtures thereof.

Amines

It may be desireable to add amine compounds which are believed to have a superficial conditioning effect. If amines are added, 0.0001–5%, preferably 0.001–3%, more preferably 0.001–2% is suggested. Suitable amines may be primary, secondary, or tertiary, or polyamines. Primary, secondary and tertiary amines exhibit the general formula $RNH_2$, $RR'NH_2$, or $RR'R''NH_2$ respectively wherein R, R', and R'' are $C_{1-50}$ straight or branched chain alkyl; substituted or unsubstituted phenyl where the substitutents are alkyl, hydroxyl, halogen, amino; and the like, as well as other amines. Examples of such amines are disclosed on pages 488–490 of the *CTFA Cosmetic Ingredient Handbook*, Second Edition, 1992.

Preferred are polyamines, particularly those having the following general formula:

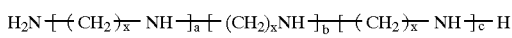

wherein each x is independently 1–10, and a, b, and c are each independently 0–20, with the proviso that at at least one of a, b, or c is 1. Most preferred is a polyamine of the formula:

This polyamine is referred to as spermine.

Humectants

The composition of the invention may also contain 0.01–20%, preferably 0.1–10%, more preferably 0.1–5% humectants. Humectants are ingredients which retard moisture loss, and are generally hygroscopic in nature. Examples of humectants include sugars such as corn syrup, fructose, glucose, glycerin, honey, inositol, maltitol, trehelose, mannitol, sorbitol, sucrose, xylitol, and the like, as well as polyethylene glycols, and derivatives thereof, butylene glycol, ethylene glycol, urea, and so on.

Emulsifiers

The composition of the invention may also contain 0.01–10%, preferably 0.01–8%, more preferably 0.1–5% of an emulsifier. Suitable emulsifiers include alkoxylated alcohols such as laureth, ceteth, deceth, pareth, oleth, steareth, and so on. Also suitable are polyethylene glycol derivatives of fatty acids, poloxamers, polyglyceryl derivatives, polysorbates, and the like.

Preservatives

The compositions may contain 0.01–10%, preferably 0.1–8%, more preferably 0.1–5% preservatives. Suitable preservatives include the parabens such as methyl, ethyl, and propyl paraben, benzoic acid, benzyl alcohol, calcium benzoate, DMDM hydantoin, diazolidinyl urea, DMDM hydantoin, methychloroisothiazolinone, quaternary ammonium compounds, and so on.

The invention also comprises a method for strengthening nails by applying the composition of the invention. The composition may be applied in the form of a nail enamel or treatment emulsion. If a nail enamel composition is used, the nails are manicured in the usual fashion and the nail enamel is left on the nails for one to five days, or the usual amount of time. The nail enamel composition may be used alone as a basecoat (i.e. clear), or the basecoat may be used in conjunction with a colored enamel which is applied on top. It is preferred that the nail enamel composition which contains the keratinous protein cross-linking agent be applied directly to the nail surface. The nail strenghthening method of the invention may also be employed by using the emulsion treatment compositions mentioned above. In that case, the emulsion is applied to the nails on a regular basis, i.e. at least once or twice a week, or as desired. Preferably, the emulsion treatment composition is applied once a week, prior to regular manicure.

The invention will be further described in connection with the following examples which are set forth for the purposes of illustration only.

EXAMPLE 1

Nail enamel compositions were made according to the following formulas:

|  | ww % | | | |
|---|---|---|---|---|
|  | 1 | 2 | 3 | 4 |
| Nitrocellulose 1/4" RS | 13.780 | 13.800 | 13.800 | 14.308 |
| Nitrocellulose, 1/2" RS | 1.893 | 1.900 | 1.900 | 1.895 |
| Glyceryl tribenzoate | 11.700 | 11.750 | 11.700 | 11.700 |
| Acetyl tri-N-butyl citrate | 3.600 | 3.650 | 3.600 | 3.700 |
| Glyceryl triacetate | 0.900 | 0.900 | 0.900 | 0.900 |
| Stearalkonium bentonite | 0.945 | 0.945 | 0.945 | 1.085 |
| Ethyl acetate | 30.150 | 29.675 | 29.680 | 29.657 |
| N butyl acetate | 26.500 | 26.600 | 26.550 | 27.900 |
| Isopropanol | 7.500 | 7.750 | 7.600 | 7.780 |
| Tetrabutylphenyl hydroxybenzoate | 0.900 | 0.900 | 0.900 | 0.900 |
| Phosphoric acid | 0.025 | 0.025 | 0.025 | 0.025 |

-continued

|  | ww % | | | |
|---|---|---|---|---|
|  | 1 | 2 | 3 | 4 |
| Malic acid | 0.010 | 0.010 | 0.010 | 0.010 |
| Citric acid | 0.090 | 0.090 | 0.090 | 0.090 |
| D&C Red #7, Calcium Lake | — | 0.003 | — | — |
| Titanium dioxide | 0.005 | 0.001 | — | — |
| FD&C Yellow #5 Aluminum Lake | — | 0.001 | — | — |
| Iron oxide | 0.002 | — | — | — |
| Titanium dioxide/mica | — | — | 0.250 | 1.000 |
| 1,3 dimethyl urea | 2.000 | 2.000 | 2.000 | 2.000 |

EXAMPLE 2

Nail clippings obtained from volunteer nos. 1–5 were treated with Treatment Compositions 1–7 (identified below) by first pre-soaking the clippings in water for 10 minutes, treating the nails with the appropriate composition for 10 minutes, then drying the clippings for 5 minutes. The clippings were analyzed for strength by measuring the amount of force in grams that was required to push a sewing needle having a diameter of 0.699 mm. through the clipping from a distance of 2 mm. using a Texture Analyzer Model TX-XT2, set to the following:

Pre-speed=0.5 mm/s

Test speed=0.1 mm/s

Post-speed=5.0 mm/s

Trigger setting=1.0 grams.

| Treatment Composition # | Treatment Composition |
|---|---|
| 1 | water |
| 2 | 40% DMU in water |
| 3 | 20% DMU in water |
| 4 | 10% DMU in water |
| 5 | 5% DMU in water |
| 6 | 2.5% DMU in water |
| 7 | 1.25% DMU in water |

The nail clippings were taken from volunteers who rated the condition of their nails by self-assessment. The condition of the samples is set forth below:

| Nail # | Condition of Nail |
|---|---|
| 1 | healthy, smooth |
| 2 | hard, uneven |
| 3 | healthy, hard, smooth |
| 4 | healthy, hard, smooth |
| 5 | healthy, hard, smooth |

| Nail # | Treatment | Force (grams) | % difference |
|---|---|---|---|
| 1 | 1 | 291.7 | — |
| 1 | 2 | 350.0 | 19.98 |
| 2 | 1 | 780.5 | — |
| 2 | 2 | 1204 | 54.26 |
| 3 | 1 | 499.4 | — |
| 3 | 2 | 615.1 | 23.17 |
| 4 | 1 | 1501.6 | — |
| 4 | 2 | 1469.9 | -2.11 |
| 5 | 1 | 733.0 | — |
| 5 | 2 | 981.1 | 33.85 |
| 1 | 1 | 291.8 | — |
| 1 | 3 | 252.8 | -13.50 |
| 3 | 1 | 628.6 | — |
| 3 | 3 | 730.3 | 16.18 |
| 4 | 1 | 501.3 | — |
| 4 | 3 | 572.5 | 14.20 |
| 5 | 1 | 768.7 | — |
| 5 | 3 | 939.1 | 22.17 |
| 1 | 1 | 278.4 | — |
| 1 | 4 | 304.1 | 9.23 |
| 2 | 1 | 1311.8 | — |
| 2 | 4 | 1205.9 | -8.07 |
| 3 | 1 | 874.9 | — |
| 3 | 4 | 734.8 | -16.01 |
| 4 | 1 | 609.8 | — |
| 4 | 4 | 794.5 | 30.29 |
| 5 | 1 | 575.7 | — |
| 5 | 4 | 615.2 | 6.86 |
| 1 | 1 | 306.9 | — |
| 1 | 5 | 360.8 | 17.56 |
| 2 | 1 | 1172.9 | — |
| 2 | 5 | 1319.9 | 12.53 |
| 3 | 1 | 2027.2 | — |
| 3 | 5 | 2206.6 | 8.86 |
| 4 | 1 | 1470.9 | — |
| 4 | 5 | 1235.7 | -15.99 |
| 5 | 1 | 1213.2 | — |
| 5 | 5 | 1664.5 | 37.20 |
| 1 | 1 | 1161.4 | — |
| 1 | 6 | 914.4 | -21.27 |
| 2 | 1 | 745.3 | — |
| 2 | 6 | 935.9 | 25.57 |
| 3 | 1 | 589.1 | — |
| 3 | 6 | 569.2 | -3.37 |
| 4 | 1 | 547.9 | — |
| 4 | 6 | 456.1 | -16.75 |
| 5 | 1 | 553.8 | — |
| 5 | 6 | 630.4 | 13.83 |
| 1 | 1 | 358.1 | — |
| 1 | 7 | 298.2 | -16.72 |
| 2 | 1 | 936.4 | — |
| 2 | 7 | 829.6 | -11.4 |
| 3 | 1 | 1713.9 | — |
| 3 | 7 | 1879.0 | 0.63 |
| 4 | 1 | 472.2 | — |
| 4 | 7 | 498.0 | 5.46 |
| 5 | 1 | 529.2 | — |
| 5 | 7 | 563.9 | 6.55 |

It can be seen from the above results that, in general, although not in all cases, nails treated with compositions containing DMU resulted in improved strength, i.e. an increase in force was required for the sewing needle to penetrate the nail clipping after it had been treated with a DMU-containing composition. There also appears to be a positive correlation between the amount of DMU in the composition and the amount of force required to cause penetration.

EXAMPLE 3

Further testing was conducted using nail clipping samples 1–5 as identified in Example 2. The clippings were pre-soaked for 10 minutes in water, then soaked in a treatment composition (identified below) for 10 minutes, and dried for 10 minutes.

| Treatment Composition # | Treatment Composition |
|---|---|
| 1 | water |
| 2 | 70% DMU in water |

The texture analyzer and set parameters used were the same as in Example 2.

| Nail # | Treatment | Force (grams) | % difference |
|--------|-----------|---------------|--------------|
| 1 | 1 | 1233.5 | — |
| 1 | 2 | 1256.6 | 1.87 |
| 2 | 1 | 498.1 | — |
| 2 | 2 | 554.3 | 11.28 |
| 3 | 1 | 634.7 | — |
| 3 | 2 | 1252 | 97.26 |
| 4 | 1 | 405 | — |
| 4 | 2 | 645.8 | 59.45 |
| 5 | 1 | 583.2 | — |
| 5 | 2 | 968.3 | 66.03 |

The above results illustrate that, in general, when nail clippings are treated with a composition containing 70% DMU, the nails exhibit improved resistance to penetration (i.e. are stronger) than nails which are treated only with water.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

We claim:

1. A composition for application to solid, keratinous surfaces comprising, by weight of the total composition:
   0.01–80% of a thio-free keratinous protein cross-linking agent,
   1–75% of a solvent, and
   0.01–35% of a film former.

2. The composition of claim 1 wherein the thio-free keratinous protein cross-linking agent is a compound of the formula:

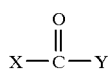

wherein X and Y are each independently halogen, $C_{1-20}$ straight or branched chain alkyl, alkoxy, aryloxy, or NRR' wherein R and R' are each independently hydrogen, halogen, $C_{1-20}$ straight or branched chain alkyl, alkoxy, aryloxy, with the proviso that at least one of R or R' is an alkyl group.

3. The composition of claim 2 wherein X and Y are NRR'.

4. The composition of claim 3 wherein each R is H, and each R' is independently a $C_{1-10}$ straight or branched chain alkyl.

5. The composition of claim 4 wherein each R is H and each R' is methyl, and the compound is 1,3-dimethyl urea.

6. The composition of claim 1 wherein the solvent is aqueous or non-aqueous.

7. The composition of claim 6 wherein the non-aqueous solvent is one or more of an aliphatic or aromatic ketone, an aliphatic or aromatic alcohol, a glycol ether, or an ester formed by the reaction of $C_{1-10}$ alkanols and carboxylic acids.

8. The composition of claim 7 wherein the non-aqueous solvent is one or more of an aliphatic or aromatic alcohol, or an ester formed by the reaction of $C_{1-10}$ alkanols and carboxylic acids.

9. The composition of claim 1 wherein the film former is a cellulosic film former.

10. The composition of claim 9 wherein the film former is one or more of nitrocellulose, cellulose acetate, cellulose acetate butyrate, cellulose acetate isobutyrate, cellulose acetate propionate, cellulose acetate propionate carboxylate, or cellulose.

11. The composition of claim 1 wherein the film former is an acrylate or methacrylate homo- or copolymer.

12. A water/oil emulsion for application to solid, keratinous surfaces comprising, by weight of the total composition:
   0.01–80% of a thio-free keratinous protein cross-linking agent,
   1–95% water,
   1–75% oil.

13. A method for strengthening solid keratinous surfaces comprising applying to said surfaces a composition comprising, by weight of the total composition:
   0.01–80% of a keratinous protein cross-linking agent,
   1–75% of a solvent, and
   0.01–35% of a film former.

* * * * *